(12) United States Patent
Kawata et al.

(10) Patent No.: US 12,004,887 B2
(45) Date of Patent: *Jun. 11, 2024

(54) RADIATION DIAGNOSIS DEVICE WITH A FIRST DETECTOR DETECTING CHERENKOV LIGHT AND A SECOND DETECTOR DETECTING ENERGY INFORMATION OF RADIATION

(71) Applicant: CANON MEDICAL SYSTEMS CORPORATION, Otawara (JP)

(72) Inventors: Go Kawata, Nagareyama (JP); Hiroaki Nakai, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 304 days.

This patent is subject to a terminal disclaimer.

(21) Appl. No.: 17/162,043

(22) Filed: Jan. 29, 2021

(65) Prior Publication Data

US 2021/0236073 A1      Aug. 5, 2021

(30) Foreign Application Priority Data

Jan. 31, 2020  (JP) ................................. 2020-014410
Jan. 22, 2021  (JP) ................................. 2021-008503

(51) Int. Cl.
*A61B 6/00*        (2006.01)
*A61B 6/03*        (2006.01)
(Continued)

(52) U.S. Cl.
CPC ............ *A61B 6/037* (2013.01); *A61B 6/4241* (2013.01); *A61B 6/4258* (2013.01);
(Continued)

(58) Field of Classification Search
CPC ......... A61B 6/037; A61B 6/42; A61B 6/4208; A61B 6/4241; A61B 6/4258;
(Continued)

(56) References Cited

U.S. PATENT DOCUMENTS 3,718,818 A * 2/1973 von Arx ................. G01T 1/22
                                                      250/361 R
7,485,872 B2 * 2/2009 Frisch ....................... G01T 1/22
                                                      250/397
(Continued)

FOREIGN PATENT DOCUMENTS

JP       2017-191086 A    10/2017
WO  WO 2010/085139 A1    7/2010

OTHER PUBLICATIONS

Ota et al., "Coincidence time resolution of 30 ps FWHM using a pair of Cherenkov-radiator-integrated MCP-PMTs", Physics in Medicine & Biology, vol. 64, 2019, 7 pages.
(Continued)

*Primary Examiner* — Allen C. Ho
(74) *Attorney, Agent, or Firm* — Oblon, McClelland, Maier & Neustadt, L.L.P.

(57) ABSTRACT

A radiation diagnosis device according to an embodiment includes a first detector and a second detector. The first detector detects Cherenkov light generated when a radiation passes. The second detector is provided to face the first detector on a side farther from a source of generating the radiation and detects the energy information of the radiation.

14 Claims, 10 Drawing Sheets

(51) Int. Cl.
*A61B 6/42* (2024.01)
*G01T 1/16* (2006.01)
*G01T 1/20* (2006.01)
*G01T 1/22* (2006.01)
*G01T 1/29* (2006.01)

(52) U.S. Cl.
CPC .......... *A61B 6/4266* (2013.01); *A61B 6/4275* (2013.01); *A61B 6/482* (2013.01); *A61B 6/5205* (2013.01); *A61B 6/5282* (2013.01); *G01T 1/1603* (2013.01); *G01T 1/2018* (2013.01); *G01T 1/22* (2013.01); *G01T 1/2985* (2013.01)

(58) Field of Classification Search
CPC ....... A61B 6/4266; A61B 6/4275; A61B 6/52; A61B 6/5205; A61B 6/03; A61B 6/032; A61B 6/035; A61B 6/482; G01T 1/16; G01T 1/1603; G01T 1/1606; G01T 1/161; G01T 1/2006; G01T 1/2018; G01T 1/20181; G01T 1/20182; G01T 1/20183; G01T 1/20184; G01T 1/20185; G01T 1/20186; G01T 1/20187; G01T 1/20188; G01T 1/22; G01T 1/29; G01T 1/2907; G01T 1/2914; G01T 1/2921; G01T 1/2928; G01T 1/2935; G01T 1/2985; G01T 1/20
USPC ........... 378/5, 10, 19, 62, 98.8, 98.9; 250/363.02, 363.03, 363.04, 370.09, 250/370.1
See application file for complete search history.

(56) References Cited

U.S. PATENT DOCUMENTS

| | | | | |
|---|---|---|---|---|
| 8,063,379 B2* | 11/2011 | Suhami | ..................... | G01T 5/02 250/370.09 |
| 8,604,440 B2* | 12/2013 | Frisch | ..................... | G01T 1/363 250/367 |
| 8,674,312 B2* | 3/2014 | Szupryczynski | ......... | G01T 1/22 250/366 |
| 8,822,935 B2* | 9/2014 | Frach | .................. | H03M 1/0827 327/24 |
| 9,029,789 B2* | 5/2015 | Shibuya | ................ | G01T 1/2985 250/367 |
| 9,176,241 B2* | 11/2015 | Frach | .................... | G01T 1/2018 |
| 9,464,997 B2* | 10/2016 | Li | .............. | G01T 1/22 |
| 9,677,931 B2* | 6/2017 | Shaber | ...................... | G01J 1/44 |
| 9,726,768 B2* | 8/2017 | Friedman | .............. | H01L 31/115 |
| 10,078,141 B2* | 9/2018 | Solf | ........................ | G01T 1/171 |
| 10,274,610 B2* | 4/2019 | Nelson | ................. | G01T 1/2002 |
| 10,281,594 B2* | 5/2019 | Benlloch Baviera | ..... | G01T 1/17 |
| 10,314,551 B2* | 6/2019 | Galbiati | .................. | G01T 1/023 |
| 10,816,682 B2* | 10/2020 | Ota | ..................... | G01T 1/363 |
| 10,823,861 B2* | 11/2020 | Ferenc | ................... | A61B 6/037 |
| 10,925,557 B2* | 2/2021 | Suyama | ................. | G01T 1/247 |
| 10,940,332 B2* | 3/2021 | Zhang | .................. | A61N 5/1071 |
| 10,996,348 B2* | 5/2021 | Ota | ............................ | G01T 1/20 |
| 11,185,297 B2* | 11/2021 | Vallgren | ................ | A61B 6/037 |
| 11,448,780 B2* | 9/2022 | Ilisie | ..................... | G01T 1/1642 |
| 11,684,321 B2* | 6/2023 | Kawata | ................ | A61B 6/4275 250/363.04 |
| 2011/0001049 A1 | 1/2011 | Shibuya et al. | | |
| 2018/0136344 A1 | 5/2018 | Nelson et al. | | |
| 2018/0252825 A1 | 9/2018 | Benlloch Baviera et al. | | |
| 2019/0324161 A1 | 10/2019 | Ota | | |
| 2020/0326438 A1 | 10/2020 | Ota et al. | | |

OTHER PUBLICATIONS

Studen et al., "Impact of the ring resolution on the performance of the dual ring high resolution silicon PET", IEEE NSS-MIC. Conference Record., 2017, 4 pages.

Extended European Search Report dated Jun. 7, 2021 in European Patent Application No. 21154394.7, 8 pages.

Sun Il Kwon, et al., "Bismuth Germanate Coupled to Near Ultraviolet Silicon Photomultipliers for Time-of Flight PET" Physics in Medicine and Biology, Institute of Physics Publishing, vol. 61, No. 18, XP020308552, Sep. 2, 2016, pp. L38-L47.

Office Action issued Jan. 26, 2024, in corresponding Chinese Patent Application No. 202110124712.4 with English translation, 11 pages.

* cited by examiner

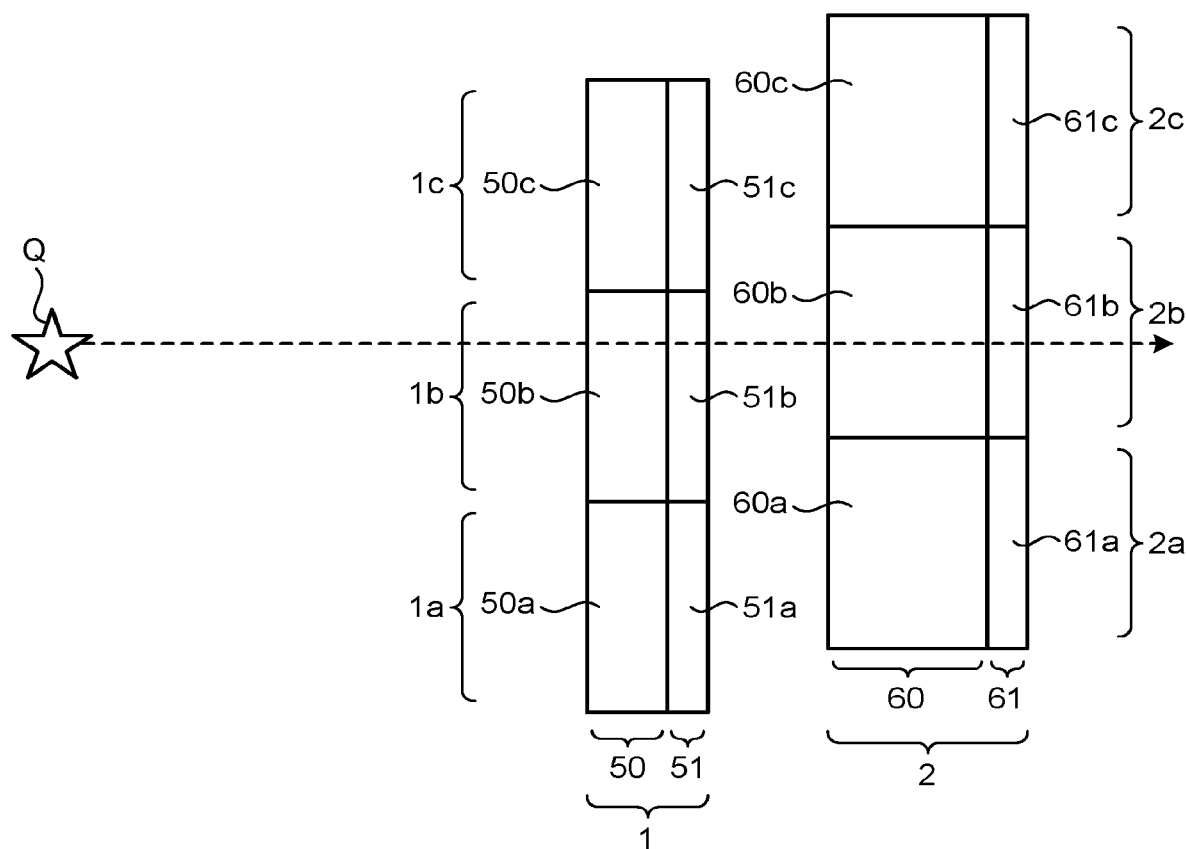

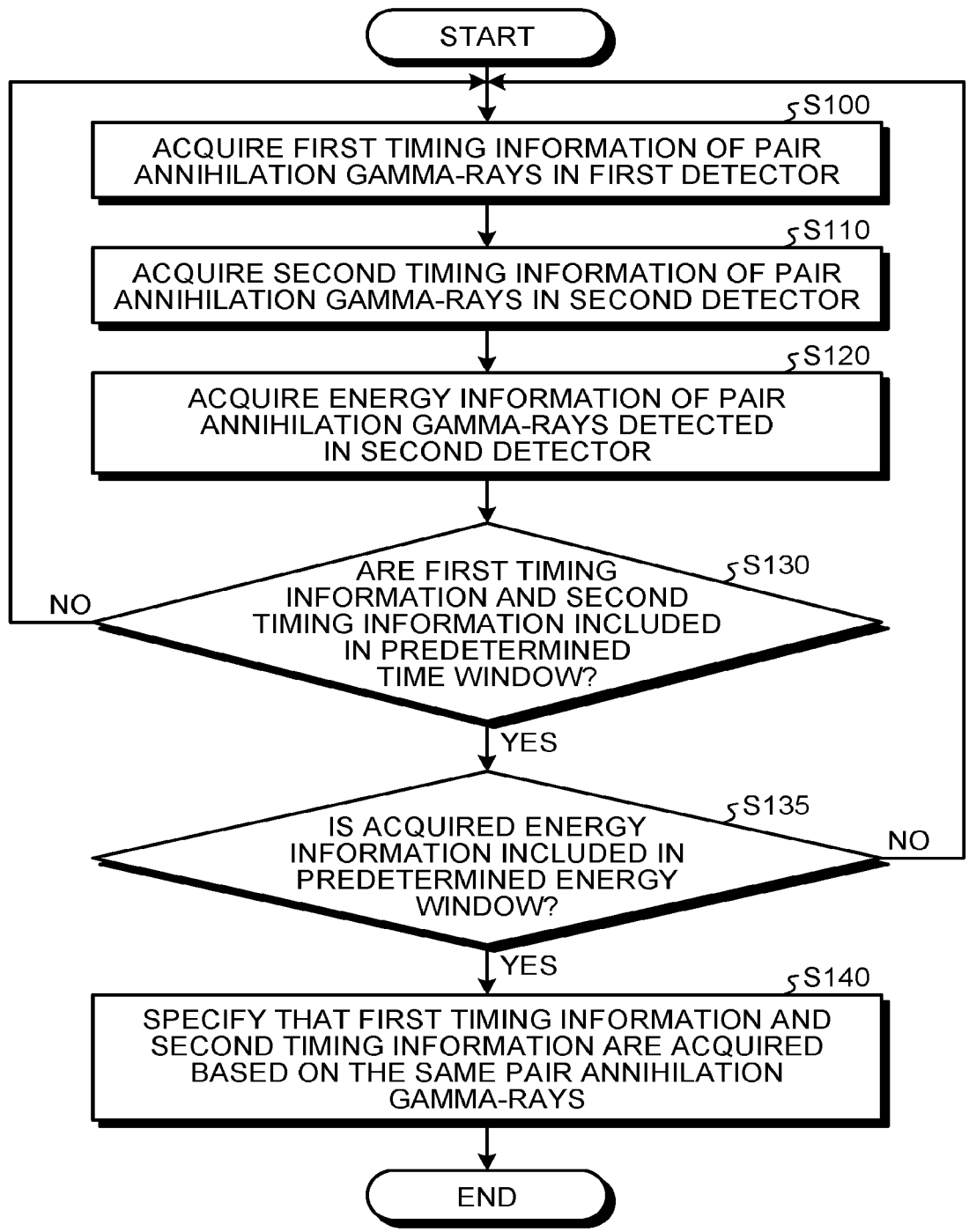

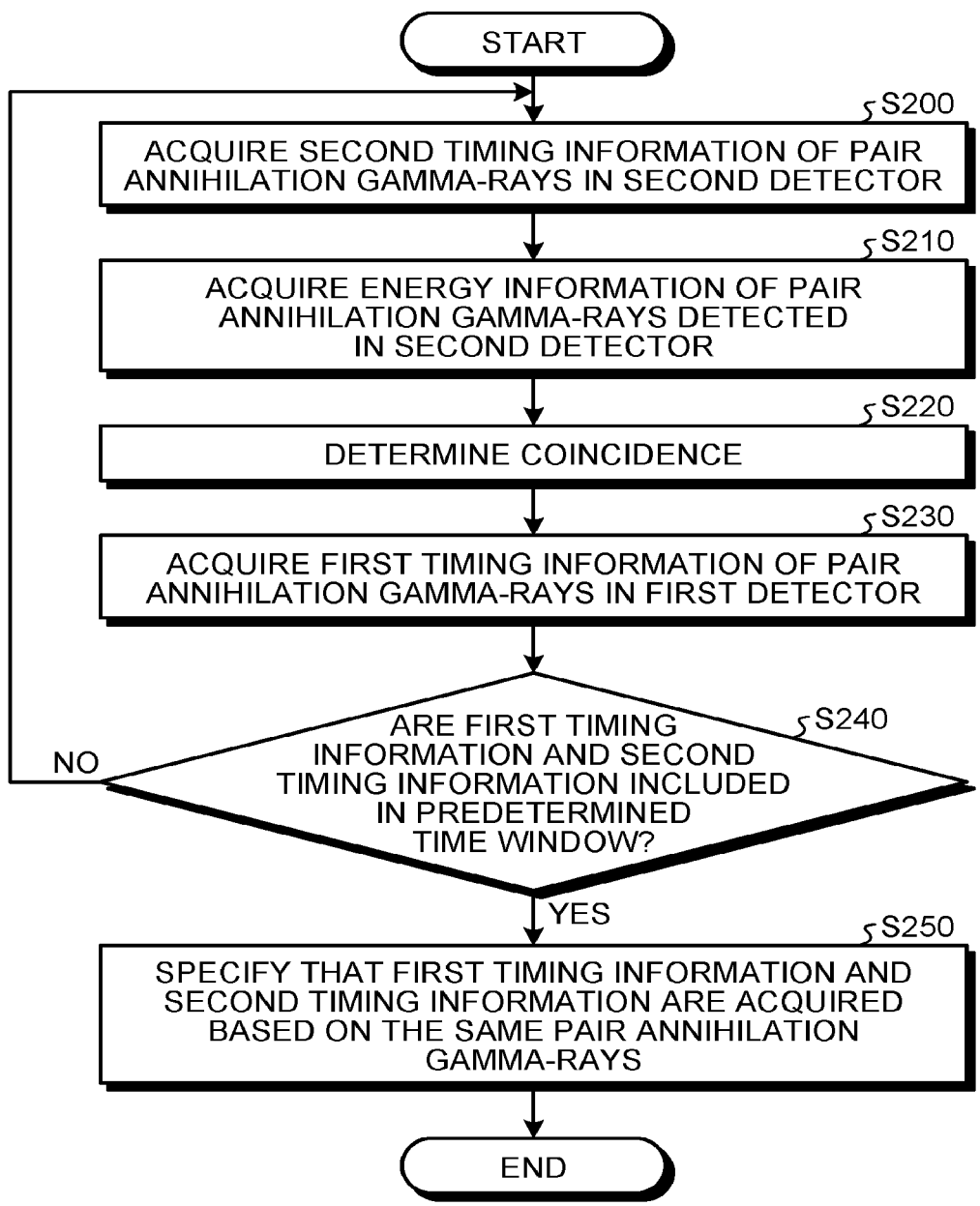

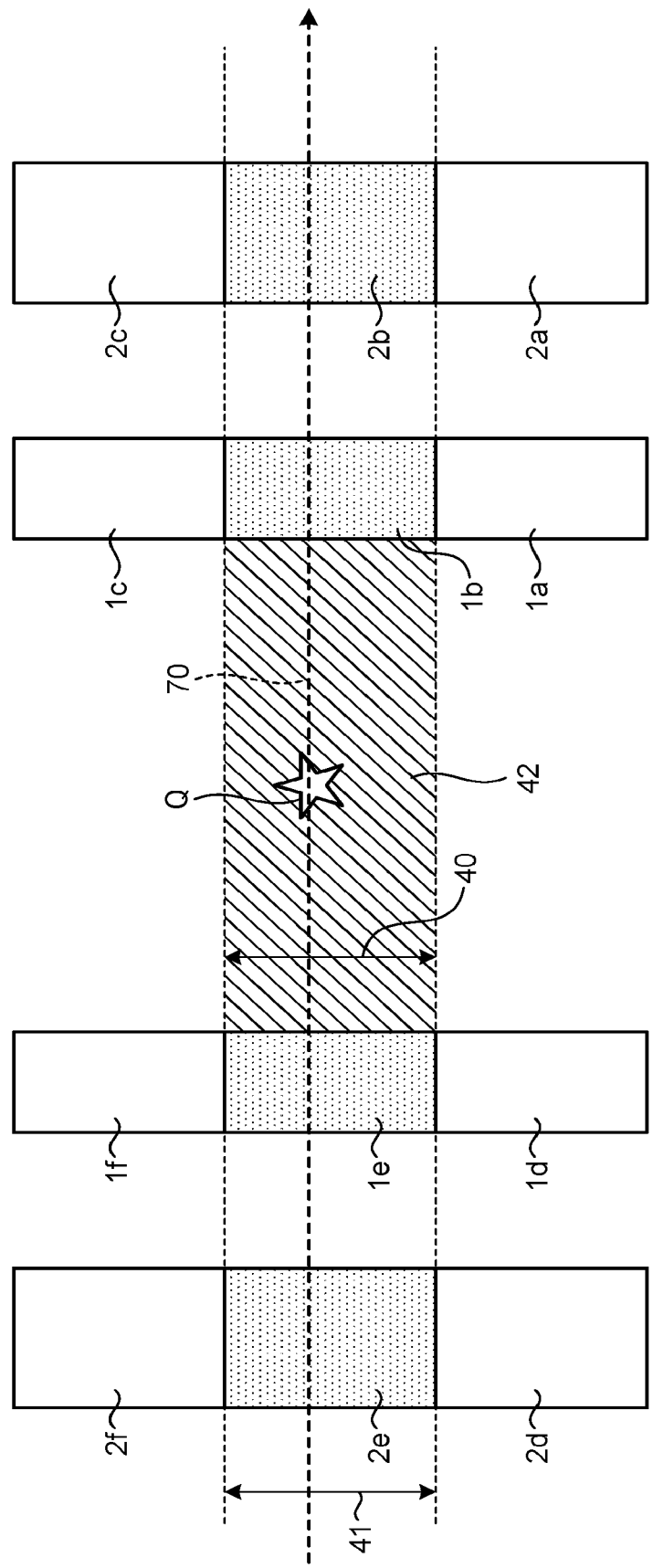

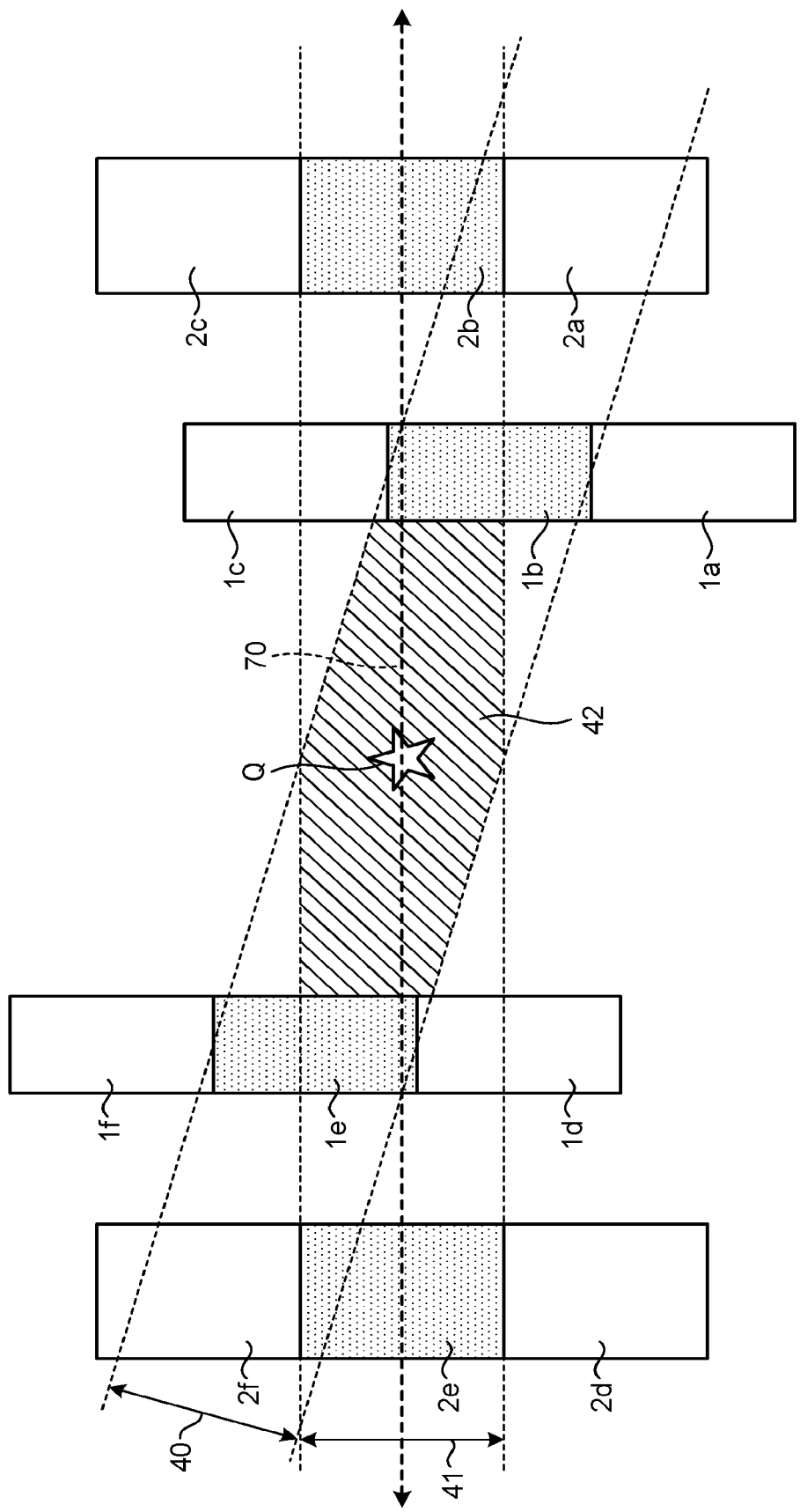

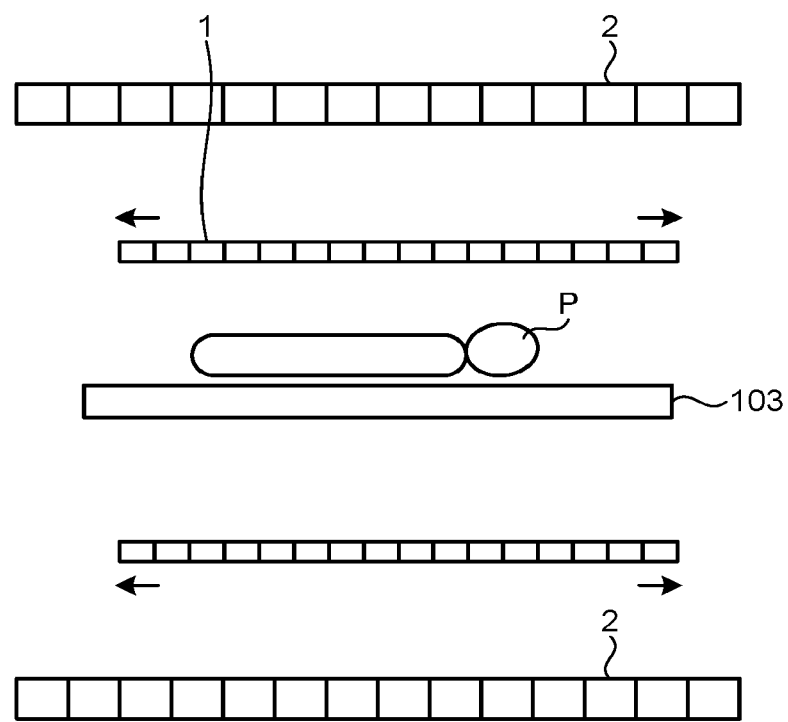

RADIATION DIAGNOSIS DEVICE WITH A FIRST DETECTOR DETECTING CHERENKOV LIGHT AND A SECOND DETECTOR DETECTING ENERGY INFORMATION OF RADIATION

CROSS-REFERENCE TO RELATED APPLICATIONS

This application is based upon and claims the benefit of priority from Japanese Patent Application No. 2020-014410, filed on Jan. 31, 2020; and Japanese Patent Application No. 2021-008503, filed on Jan. 22, 2021; and the entire contents of which are incorporated herein by reference.

FIELD

Embodiments disclosed herein relate to a radiation diagnosis device and a radiation diagnosis method.

BACKGROUND

As a radiation diagnosis device, a positron emission tomography (PET) device has been known. In the PET device, by detecting a scintillation light generated when a pair of annihilation gamma rays enter a scintillator, a pair-annihilation position of a positron is specified and by using this, a medical image is generated, the pair of annihilation gamma rays being generated in a pair when the positron emitted from a radiopharmaceutical marked with a positron emission radionuclide and electrons annihilate, The scintillation light, however, is the light that is re-emitted in a transition process in which an excitation state produced by the pair annihilation gamma-rays returns to a ground state over time, and therefore, the response speed is relatively low and errors may occur in specifying the pair annihilation position of the positron.

BRIEF DESCRIPTION OF THE DRAWINGS

FIG. 2 is a diagram for describing an example of detectors included in the radiation diagnosis device according to the embodiment;

FIG. 5 is a flowchart for describing the procedure of a process in the radiation diagnosis device according to the embodiment;

FIG. 6 is a flowchart for describing the procedure of a process in the radiation diagnosis device according to the embodiment;

FIG. 7 is a diagram for describing the arrangement of the detectors in the radiation diagnosis device according to the embodiment;

FIG. 8 is a diagram for describing the arrangement of the detectors in the radiation diagnosis device according to the embodiment; and FIG. 9 is a diagram for describing a radiation diagnosis device according to another embodiment.

DETAILED DESCRIPTION

A radiation diagnosis device according to one embodiment includes a first detector and a second detector. The first detector detects Cherenkov light that is generated when a radiation passes. The second detector is provided to face the first detector on a side farther from a source of generating the radiation and detects the energy information of the radiation.

The radiation diagnosis device, a PET device, and a radiation diagnosis method according to the embodiment are hereinafter described in detail with reference to the drawings.

Embodiment

First, regarding a structure of the radiation diagnosis device according to the embodiment, a PET device is described as one example with reference to FIG. 1 to FIG. 6.

Figure 1:
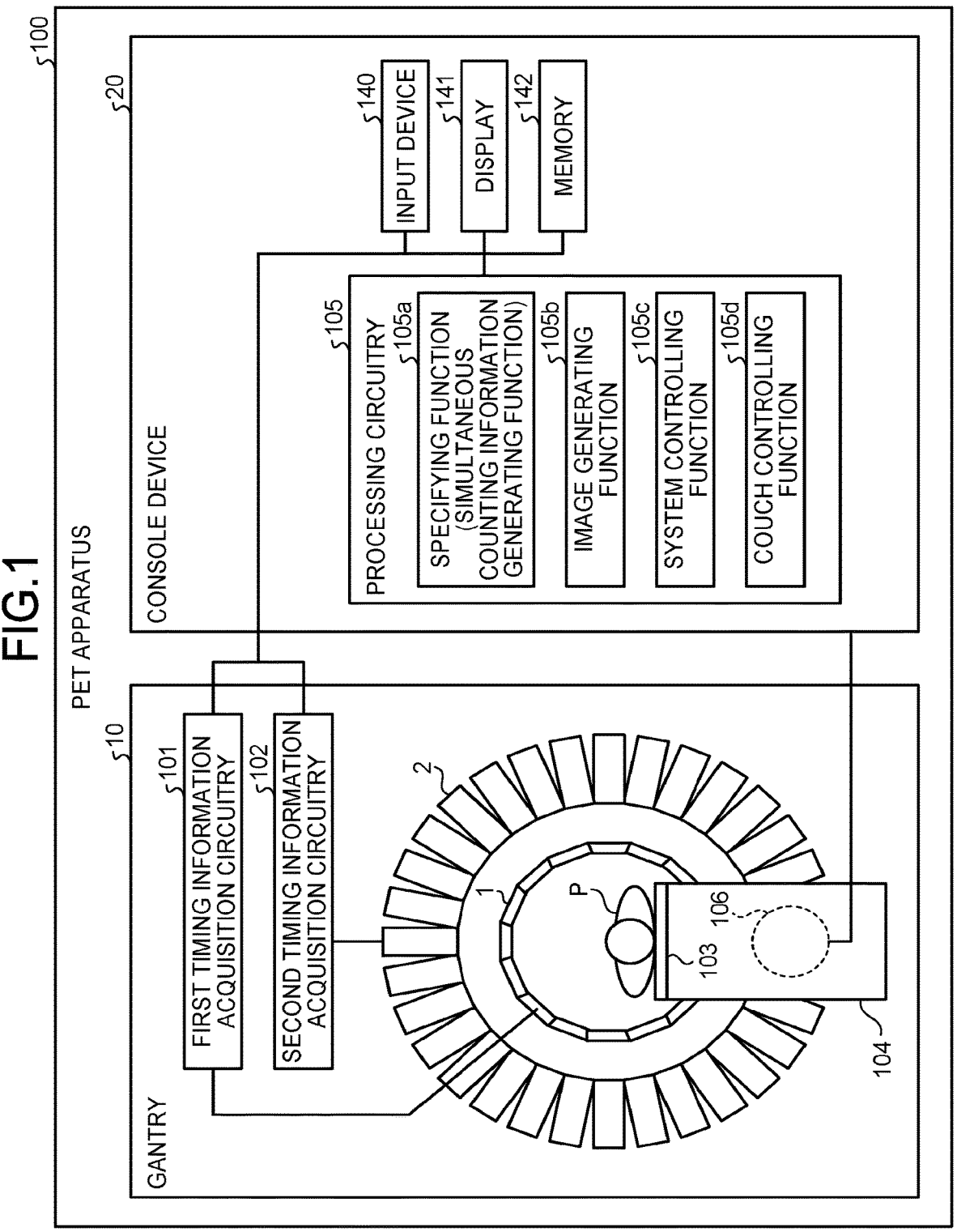
FIG. 1 is a diagram illustrating a radiation diagnosis device according to one embodiment.

FIG. 1 is a diagram illustrating a structure of a PET device 100 according to the embodiment. As illustrated in FIG. 1, the PET device 100 according to the embodiment includes a gantry 10 and a console device 20.

The gantry 10 detects a pair of annihilation gamma-rays released from positrons in a subject P using a first detector 1 configured to detect Cherenkov light and a second detector 2 configured to detect scintillation light, the first detector 1 and the second detector 2 being provided in a ring-like form so as to encompass the subject P. In addition, the gantry 10 generates counting information from output signals of the first detector 1 and the second detector 2 by first timing information acquisition circuitry 101 and second timing information acquisition circuitry 102.

More specifically, the gantry 10 includes a couchtop 103, a couch 104, a couch driving unit 106, the first detector 1 that detects Cherenkov light, the second detector 2 that detects the scintillation light, the first timing information acquisition circuitry 101 that generates the counting information from the first detector 1, and the second timing information acquisition circuitry 102 that generates the counting information from the second detector 2.

First, the first detector 1 and the second detector 2 are described with reference to FIG. 1 and FIG. 2.

The first detector 1 is a detector that acquires the counting information about pair annihilation gamma-rays released from the positrons in the subject P in a manner that the first detector 1 detects the Cherenkov light that is the light of a shock wave generated when a charged particle, which is generated from the interaction of the pair annihilation gamma-rays released from the positrons in the subject P with a light emitter (radiator) inside, moves faster than the phase velocity of the light in the medium. That is to say, the first detector 1 detects the Cherenkov light generated when the radiation passes.

The first detector 1 that is the detector of the pair annihilation gamma-rays using the Cherenkov light is inferior to the detector of the pair annihilation gamma-rays using the scintillation light in terms of sensitivity to energy. However, since the Cherenkov light is generated in a very short time compared to the scintillation light, the response characteristic is excellent. For this reason, the first detector 1 that employs a method of detecting the Cherenkov light has a characteristic of being superior to the detector that employs a method of detecting the scintillation light in terms of time resolution.

In other words, the first detector 1 that is the detector configured to detect the Cherenkov light has the characteristic being advantageous in terms of time resolution over the second detector 2 that is the detector configured to detect the scintillation light. On the other hand, the second detector 2 that is the detector configured to detect the scintillation light has a characteristic of being advantageous in terms of energy resolution over the first detector 1 that is the detector configured to detect the Cherenkov light.

Therefore, the radiation diagnosis device according to the embodiment generates the counting information using the first detector 1 and the second detector 2. Thus, the counting information maintaining the high time resolution while keeping the energy resolution can be generated.

FIG. 2 is a schematic diagram of the arrangement of the first detector 1 and the second detector 2. In FIG. 2, a generation point Q of the pair annihilation gamma-rays is illustrated. Here, the first detector 1 is formed of a plurality of pixels 1a, 1b, 1c, and the like.

Note that one pixel of the detector refers to the minimum separation unit of the position resolution of the detector. For example, in a case where the light detection elements detect the Cherenkov light generated at different positions, each of the light detection elements functions as a detector of one pixel. On the contrary, in a case where the light detection elements detect the Cherenkov light generated at the same position, the light detection elements collectively function as a detector of one pixel. In FIG. 2, only three pixels 1a, 1b, and 1c are illustrated as the pixels of the first detector 1; however, in fact, many pixels are arranged as these pixels of the detector are arranged in a ring-like form. FIG. 2 is merely a schematic diagram illustrating the arrangement of the first detector 1 and the second detector 2, and the size of the pixels 1a, 1b, and 1c of the detector is different from that of the actual detector.

In the embodiment, one light detection element may be configured as a light detection element of multiple pixels.

In the example illustrated in FIG. 1, the detector 1 is formed by a plurality of detector blocks; however, one pixel in FIG. 2 means a pixel unit by which the position of the generation of the Cherenkov light can be separated, and may be a unit smaller than the detector block illustrated in FIG. 1. That is to say, each detector block of the first detector 1 that is configured as the ring-like form in FIG. 1 may be formed of a plurality of pixels.

Back to FIG. 2, the first detector 1 includes a light emitter 50 formed of a medium that generates the Cherenkov light by the interaction with the pair annihilation gamma-rays that are the radiation released from the positrons in the subject P, and a light detection element 51 that detects the generated Cherenkov light. That is to say, the pixels 1a, 1b, and 1c included in the first detector 1 include light emitters (radiators) 50a, 50b, and 50c, and light detection elements 51a, 51b, and 51c that detect the generated Cherenkov light, respectively.

Here, the light emitter (radiator) 50 in the first detector 1 is formed of, for example, a medium containing an atom with a large atomic number having a property of easily causing a photoelectric effect by the interaction with the incident radiation and while not easily generating the scintillation light that becomes noise; for example, bismuth germanium oxide (BGO), and lead compounds such as lead glass ($SiO_2$+PbO), lead fluoride ($PbF_2$), and PWO ($PbWO_4$) are usable. In other words, the light emitter 50 in the first detector 1 is formed of a medium that easily causes the photoelectric effect but suppresses the scintillation due to the radiation, for example.

The light detection element 51 detects the generated Cherenkov light. The light detection element 51 is a silicon photomultiplier (SiPM) that is an avalanche photo diode (APD) array in which the size of the respective pixels is reduced to about several tens of micrometers, and operates in a Geiger mode. In another example, the light detection element 51 is formed of a plurality of pixels that perform the photoelectric conversion, and each pixel is formed of a single photon avalanche diode (SPAD).

Here, the thickness of the light emitter 50 in the first detector 1 may be designed to be smaller than the thickness of a scintillator 60 provided in the second detector 2, for example, in order to prevent the gamma-rays from losing its entire energy in the light emitter. Thus, the pair annihilation gamma-rays that are produced as a pair enter the second detector 2 with most of the energy kept, while the Cherenkov light is generated in the first detector 1, and the scintillation light can be generated in the second detector 2.

Moreover, the pixel size of the light emitter 50 in the first detector 1 can be made smaller than the pixel size of the scintillator 60 in the second detector 2, for example. Thus, the positional resolution of the data obtained from the first detector 1 can be increased relatively. Furthermore, the detector column length of the first detector may be shorter than that of the second detector.

Back to FIG. 1, the second detector 2 is the detector that detects the radiation by detecting the scintillation light (fluorescence) that is the light released again when the material that has become excited by the interaction of the annihilation gamma-rays released from the positrons in the subject P with the light emitter (scintillator) transits to the ground state again. The second detector 2 is also a detector that detects the energy information of the radiation of the annihilation gamma-rays released from the positrons in the subject P.

The second detector 2 is provided to face the first detector 1 that detects the Cherenkov light on a side farther from a source of generating the radiation, that is, the annihilation gamma-rays released from the positrons in the subject P. In another example, the second detector 2 is provided in a manner that a plurality of detector blocks are disposed so as to encompass, in the ring-like form, the first detector 1 that is provided to encompass the subject P in the ring-like form. In still another example, the second detector 2 is the detector with a ring-like shape, which is similar to the first detector 1, and the diameter of the second detector 2 is larger than that of the first detector 1.

As described above, the generation of the scintillation light is a slower process than the generation of the Cherenkov light. On the other hand, most part of the energy of the annihilation gamma-rays is converted into the scintillation light; therefore, from the viewpoint of measuring the energy of the annihilation gamma-rays, the second detector 2 using the scintillation light is advantageous over the first detector 1 using the Cherenkov light.

Back to FIG. 2 again, the second detector 2 is formed of a plurality of pixels 2a, 2b, 2c, and the like.

Note that one pixel of the detector refers to the minimum separation unit of the positional resolution of the detector, which is similar to the case of the first detector 1. For example, in a case where the light detection elements detect the scintillation light generated at different positions, each of the light detection elements serves as a detector of one pixel. On the contrary, in a case where the light detection elements detect the scintillation light generated at the same position, the light detection elements collectively serve as a detector of one pixel. Similar to the case of the first detector 1, only three pixels 2a, 2b, and 2c are illustrated as the pixels of the second detector 2; however, in reality, many pixels are arranged in the ring-like form as the pixels of the detector.

In the embodiment, in a manner similar to the first detector 1, one light detection element included in the second detector 2 may be configured as light detection elements of multiple pixels.

Note that in FIG. 1, the second detector 2 is formed of detector blocks; however, one pixel in FIG. 2 means a pixel unit by which a position of generation of the Cherenkov light can be separated, and one pixel may be a unit smaller than a unit of the detector block in FIG. 1. That is to say, each detector block of the second detector 2 in the ring-like form illustrated in FIG. 1 may be formed by a plurality of pixels.

Subsequently, as one example of a specific structure of the second detector 2, a photon counting type or Anger type detector is given. For example, the second detector 2 includes the scintillator 60 and a light detection element 61 that are illustrated in FIG. 2, and a light guide that is not illustrated. That is to say, the pixels 2a, 2b, and 2c in the second detector 2 include scintillators 60a, 60b, and 60c and light detection elements 61a, 61b, and 61c that detect the generated scintillation light, respectively.

The scintillator 60 converts the incident annihilation gamma-rays released from the positrons in the subject P into the scintillation light (scintillation photons, optical photons), and outputs the resulting light. The scintillator is formed by, for example, scintillator crystal suitable for TOF measurement or energy measurement, such as lanthanum bromide (LaBr3), lutetium yttrium oxyorthosilicate (LYSO), lutetium oxyorthosilicate (LSO), lutetium gadolinium oxyorthosilicate (LGSO), or BGO, and is arranged two-dimensionally, for example.

As the light detection element 61, for example, the aforementioned silicon photomultiplier (SiPM) or a multiplier phototube is used. The multiplier phototube includes a photoelectric cathode that receives the scintillation light and generates photoelectrons, a multistage dynode that applies an electric field that accelerates the generated photoelectrons, and an anode corresponding to an outlet from which the electrons flow out. The multiplier phototube multiplies the scintillation light output from the scintillator and converts the scintillation light into electric signals.

The light guide is formed of a plastic material with the excellent light-transmitting property or the like, and sends the scintillation light output from the scintillator to the light detection element, for example the SiPM or the multiplier phototube.

Note that the thickness of the scintillator 60 provided to the second detector 2 can be made larger than the thickness of the light emitter 50 provided to the first detector 1.

In addition, the pixel size of the scintillator 60 provided to the second detector 2 can be made larger than the pixel size of the light emitter 50 provided to the first detector 1.

Subsequently, back to FIG. 1, other structures are described.

The first timing information acquisition circuitry 101 generates the counting information from the output signal of the first detector 1, and stores the generated counting information in a memory 142 in the console device 20. Note that although not illustrated in FIG. 1, the first detector 1 is sectioned into a plurality of blocks and includes the first timing information acquisition circuitry 101 for each block.

The first timing information acquisition circuitry 101 converts the output signal of the first detector 1 into digital data and generates the counting information. This counting information includes a detection position and a detection time of the annihilation gamma-rays. For example, the first timing information acquisition circuitry 101 specifies the light detection elements that have converted the Cherenkov light into electric signals at the same timing. Then, the first timing information acquisition circuitry 101 calculates the position of center of gravity using the position of each of the specified light detection elements and the intensity of the electric signal, and specifies a detection element number (P) expressing the position of the radiator on which the annihilation gamma-rays have been incident.

Moreover, the first timing information acquisition circuit 101 specifies the detection time (T) when the first detector 1 has detected the Cherenkov light generated by the annihilation gamma-rays. Note that the detection time (T) may be either the absolute time or elapsed time since the start of the image capture. In this manner, the first timing information acquisition circuitry 101 generates the counting information including the detection element number (P) and the detection time (T).

The second timing information acquisition circuitry 102 generates the counting information from the output signal of the second detector 2, and stores the generated counting information in the memory 142 in the console device 20. Note that, in a manner similar to the first detector 1, the second detector 2 is sectioned into a plurality of blocks, and includes the second timing information acquisition circuitry 102 for each block.

The second timing information acquisition circuitry 102 converts the output signal of the second detector 2 into digital data, and generates the counting information. This counting information includes the detection position, the energy value, and the detection time of the annihilation gamma-rays. For example, the second timing information acquisition circuitry 102 specifies the light detection elements that have converted the scintillation light into electric signals at the same timing. Then, the second timing information acquisition circuitry 102 specifies the scintillator number (P) expressing the position of the scintillator on which the annihilation gamma-rays have been incident. The position of the scintillator on which the annihilation gamma-rays have been incident may be specified by the calculation of center of gravity on the basis of the position of each light detection element and the intensity of the electric signal. In the case where each element size of the scintillator and the light detection element corresponds to each other, the scintillator corresponding to the light detection element from which the output is obtained may be specified as the position of the scintillator on which the annihilation gamma-rays have been incident.

The second timing information acquisition circuitry 102 specifies the energy value (E) of the annihilation gamma-rays incident into the second detector 2 by the integral calculation of the intensity of the electric signal output from each light detection element. In addition, the second timing information acquisition circuitry 102 specifies the detection time (T) when the second detector 2 has detected the scintillation light by the annihilation gamma-rays. Note that the detection time (T) may be either the absolute time or elapsed time since the start of the image capture. In this manner, the second timing information acquisition circuitry 102 generates the counting information including the scintillator number (P), the energy value (E), and the detection time (T).

Here, P is a position of detector on which the annihilation gamma-rays have been incident.

Note that the first timing information acquisition circuitry 101 and the second timing information acquisition circuitry 102 may be formed by a circuit, for example, a central processing unit (CPU), a graphical processing unit (GPU), an application specific integrated circuit (ASIC), a programmable logic device (such as a simple programmable logic device: SPLD), a complex programmable logic device (CPLD), a field programmable gate array (FPGA), or the like. The first timing information acquisition circuitry 101 and the second timing information acquisition circuitry 102 are examples of the first information acquisition unit and the second timing information acquisition unit, respectively.

The couchtop 103 is a bed on which the subject P is placed, and is disposed on the couch 104. The couch driving unit 106 moves the couchtop 103 under the control of a couch controlling function 105d of the processing circuitry 105. For example, the couch driving unit 106 moves the couchtop 103 so that the subject P moves into an image capturing port of the gantry 10.

The console device 20 receives the operator's operation of the PET device 100 and controls the capture of the PET image, and moreover reconfigures the PET image using the counting information collected by the gantry 10. As illustrated in FIG. 1, the console device 20 includes the processing circuitry 105, an input device 140, a display 141, and the memory 142. Note that each part of the console device 20 is connected through a bus.

In the embodiment, each processing function performed by a specifying function (simultaneous counting information generating function) 105a, an image generating function 105b, a system controlling function 105c, and the couch controlling function 105d is stored in the memory 142 in the format of computer programs that are executable by the computer. The processing circuitry 105 is a processor that reads out the computer program from the memory 142 and executes the computer program so as to achieve the function corresponding to the computer program. In other words, the processing circuitry 105 that has read each computer program has each function illustrated in the processing circuitry 105 in FIG. 1. In FIG. 1, the processing functions that are performed in the specifying function (simultaneous counting information generating function) 105a, the image generating function 105b, the system controlling function 105c, and the couch controlling function 105d are achieved in one processing circuitry 105; however, the processing circuitry 105 may alternatively be configured by combining a plurality of independent processors and by executing the computer program in each processor, the processing circuitry 105 may achieve the functions. In other words, each of the aforementioned functions may be configured as the computer program and one processing circuitry 105 may execute each computer program. In another example, a particular function may be mounted in a dedicated independent computer program executing circuitry.

Note that in FIG. 1, the specifying function 105a, the image generating function 105b, the system controlling function 105c, and the couch controlling function 105d are examples of a specifying unit, an image generation unit, a system control unit, and a couch control unit, respectively.

The term "processor" used in the above description refers to a circuit such as a central processing unit (CPU), a graphical processing unit (GPU), an application specific integrated circuit (ASIC), a programmable logic device (such as a simple programmable logic device: SPLD), a complex programmable logic device (CPLD), or a field programmable gate array (FPGA). The processor achieves the function by reading out and executing the computer program saved in the memory 142.

The processing circuitry 105 causes the specifying function (simultaneous counting information generating function) 105a to generate the simultaneous counting information on the basis of the counting information about the first detector 1 that is acquired by the first timing information acquisition circuitry 101 and the counting information about the second detector 2 that is acquired by the second timing information acquisition circuitry 102, and stores the generated simultaneous counting information in the memory 142. The detailed process of the specifying function 105a is described below.

The processing circuitry 105 causes the image generating function 105b to reconfigure the PET image. Specifically, the processing circuitry 105 causes the image generating function 105b to read out the time-series list of the simultaneous counting information stored in the memory 142, and reconfigures the PET image using the read time-series list. In addition, the processing circuitry 105 stores the reconfigured PET image in the memory 142.

The processing circuitry 105 causes the system controlling function 105c to control the gantry 10 and the console device 20, thereby controlling the entire PET device 100. For example, the processing circuitry 105 causes the system control unit 105c to control the image capture in the PET device 100.

The processing circuitry 105 causes the couch controlling function 105d to control the couch driving unit 106.

The input device 140 is a mouse or a keyboard, for example, that is used to input various instructions or settings by the operator of the PET device 100, and transfers the input various instructions and settings to the processing circuitry 105. For example, the input device 140 is used to input the image capture start instruction.

The display 141 is a monitor or the like that is seen by the operator, and under the control of the processing circuitry 105, displays the respiration waveform or the PET image of the subject, and displays a graphical user interface (GUI) for receiving various instructions or settings from the operator.

The memory 142 stores various pieces of data used in the PET device 100. The memory 142 is, for example, a semiconductor memory element such as a random access memory (RAM) or a flash memory, a hard disk, or an optical disk. The memory 142 stores therein, the counting information corresponding to the information in which the scintillator number (P), the energy value (E), and the detection time (T) are associated with each other, the simultaneous counting information in which the coincidence number corresponding to the serial number of the simultaneous counting information is associated with a set of counting information, the reconfigured PET image, and the like.

Subsequently, a process of generating the simultaneous counting information in the PET device 100 according to the embodiment is described with reference to FIG. 3A to FIG. 6.

Figure 3A:
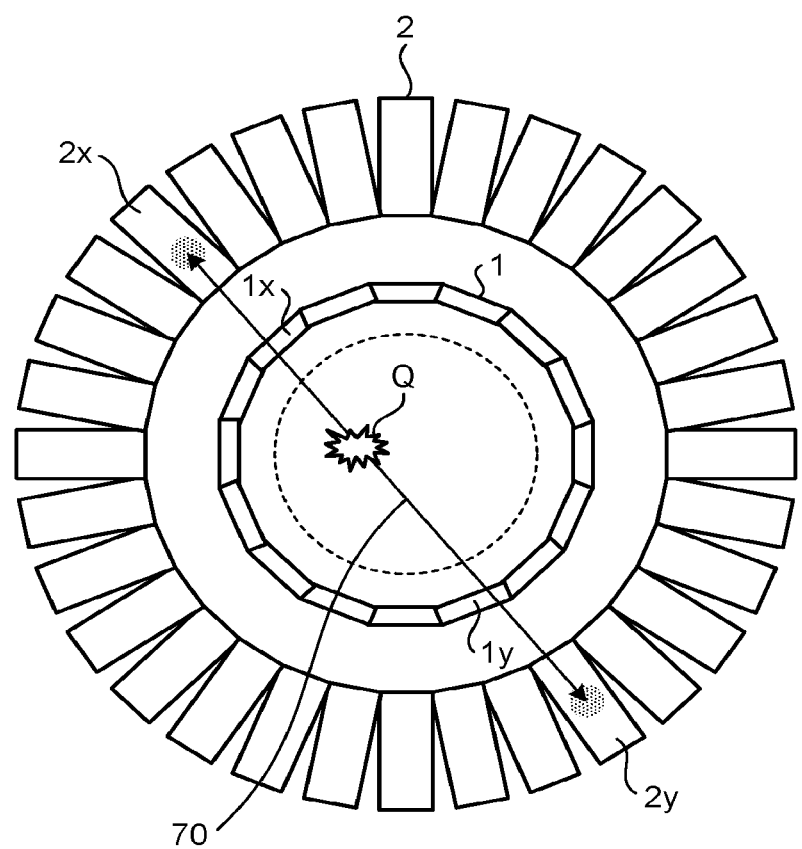
FIG. 3A and FIG. 3B are diagrams each for describing a counting process in the radiation diagnosis device according to the embodiment.

Description is hereinafter made of a case in which, as illustrated in FIG. 3A, the Cherenkov light derived from a pair of gamma-rays produced as a pair from an annihilation point Q is detected by a detector 1x and a detector 1y that correspond to the first detector 1 configured to detect the Cherenkov light and the scintillation light of a pair of gamma-rays produced as a pair from the annihilation point Q is detected by a detector 2x and a detector 2y that correspond to the second detector 2 configured to detect the scintillation light. That is to say, the processing circuitry 105 causes the specifying function 105a to generate the simultaneous counting information using the data obtained by at least two pairs of detectors: a pair of detectors that is the first detector 1 and a pair of detectors that is the second detector 2.

Figure 3B:
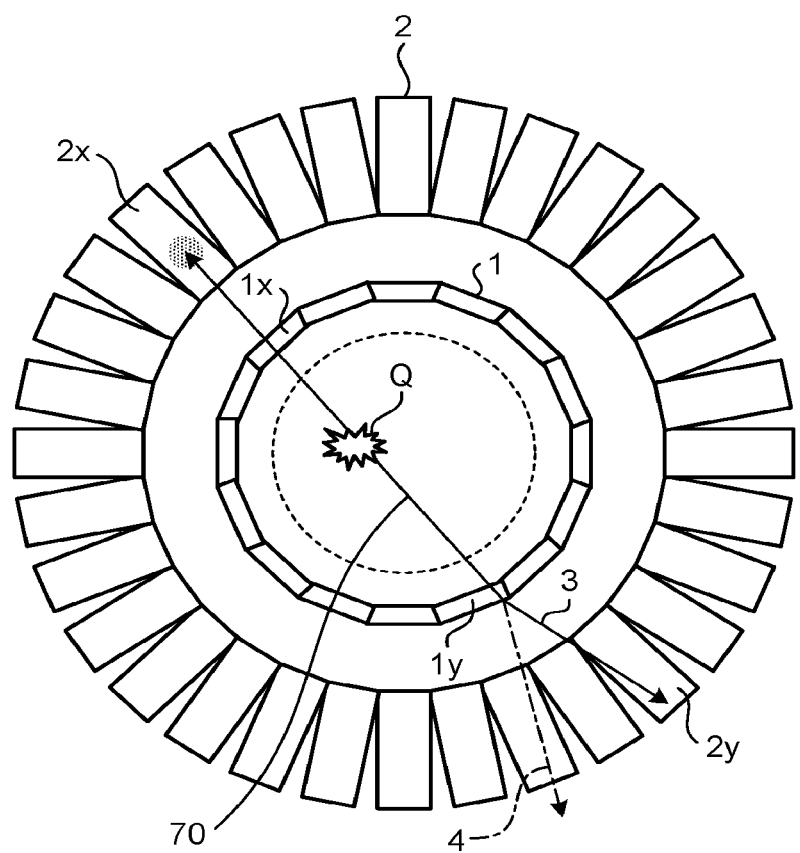

Note that, in fact, as illustrated in FIG. 3B, when Compton scattering occurs in the first detector 1 that detects the Cherenkov light and a recoil electron 4 is generated thereby, the trajectory of a pair of gamma-rays produced as a pair from the pair annihilation Q is deviated a little from the trajectory of the gamma-rays inside the first detector 1 as expressed by a gamma-ray trajectory 3 after Compton scattering.

Figure 4:
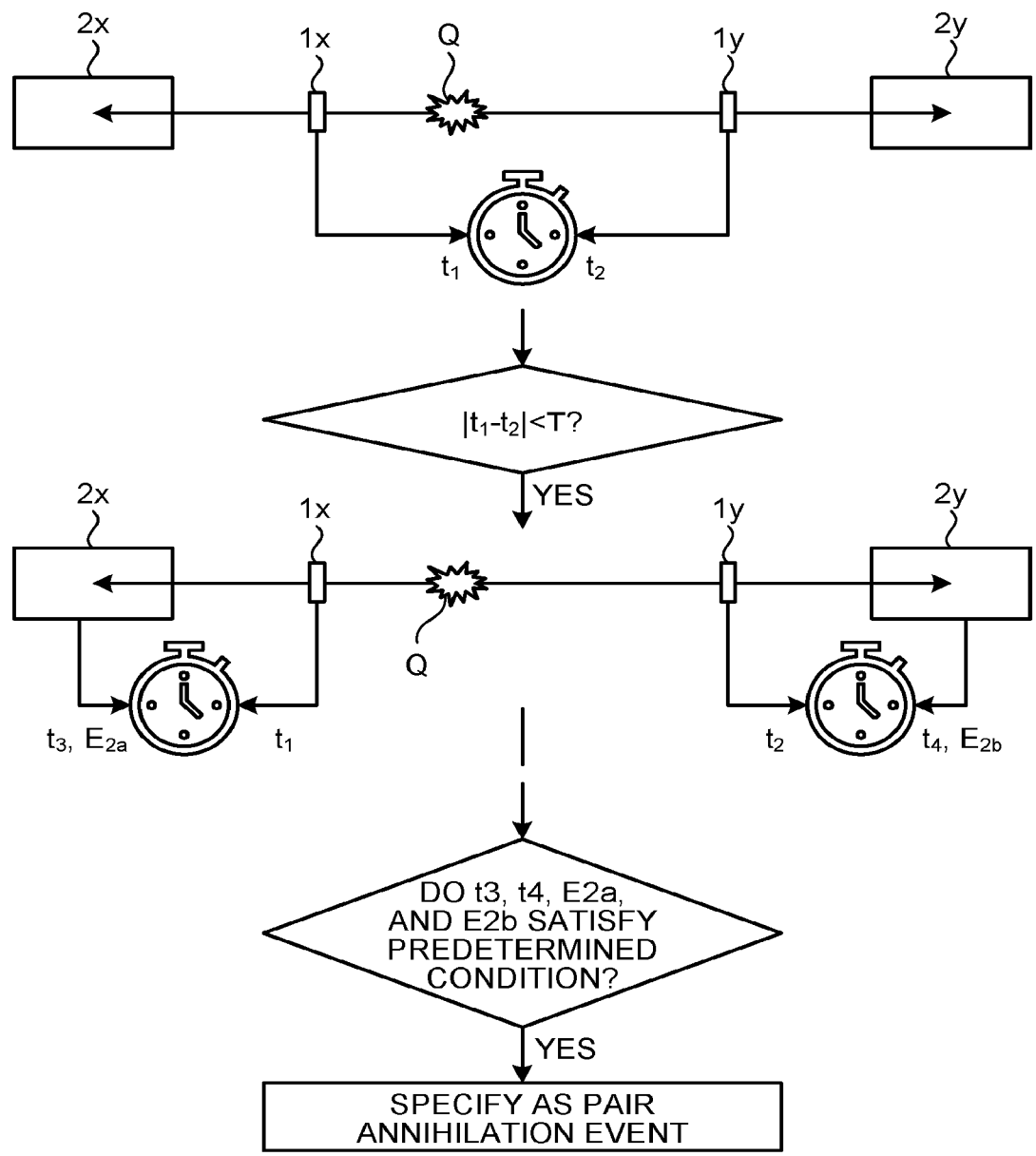
FIG. 4 is a diagram for describing the counting process in the radiation diagnosis device according to the embodiment.

Subsequently, the generation of the simultaneous counting information of the gamma-rays is described with reference to FIG. 4. As the method of generating the simultaneous counting information, for example, the following two methods are considered: a method as illustrated in FIG. 4 in which the simultaneous counting is performed in the first detector 1 that is the detector configured to detect the Cherenkov light and then, by referring to the data obtained in the second detector 2 that is the detector configured to detect the scintillation light, the final simultaneous counting information is generated; and a method in which the simultaneous counting is performed in the second detector 2 that is the detector configured to detect the scintillation light and then, by referring to the data obtained in the first detector 1 that is the detector configured to detect the Cherenkov light, the final simultaneous counting information is generated. The former method is described with reference to FIG. 4 and FIG. 5, and the latter method is described with reference to FIG. 6.

First, as the method of generating the simultaneous counting information, the method of performing the simultaneous counting in the first detector 1 that is the detector configured to detect the Cherenkov light first is described with reference to FIG. 4 and FIG. 5. In this method, a process of generating the simultaneous counting information is performed using the data obtained from the first detector 1 with the high time resolution first. Specifically, as illustrated in FIG. 4, the processing circuitry 105 performs the process using the detector 1x and the detector 1y that are the first detector, and after that, performs the process using the detector 2x and the detector 2y that are the second detector, and specifies whether the event is the pair annihilation event and if it is the pair annihilation event, specifies the pair annihilation position and time. FIG. 5 is a flowchart expressing this process.

At step 5100, the first timing information acquisition circuitry 101 acquires the first timing information of the pair annihilation gamma-rays in the first detector 1. In addition, the first timing information acquisition circuitry 101 transmits the acquired first timing information to the processing circuitry 105 in the console device 20. Here, the first timing information of the pair annihilation gamma-rays in the first detector corresponds to, for example, a list of the detection element number (P) and the detection time (T).

Note that one typical example of the detection time (T) is the time when the light detection element 51 of the first detector 1 has observed the Cherenkov light. However, the embodiment is not limited to this example, and the detection time may be the estimated value of the time when the Cherenkov light is generated by the interaction between the pair annihilation gamma-rays and the light emitter 50 of the first detector 1 that is estimated based on the time when the light detection element 51 of the first detector 1 has observed the Cherenkov light, for example. In the first detector 1, the estimated time of the time when the Cherenkov light is generated by the interaction between the pair annihilation gamma-rays and the light emitter 50 of the first detector 1 and the time when the light detection element 51 of the first detector 1 has observed the Cherenkov light are approximately the same. As described above, the detection time (T) may be either the absolute time or elapsed time since the start of the image capture.

As illustrated in FIG. 4, the first timing information acquisition circuitry 101 acquires a pair of pieces of first timing information of the pair annihilation gamma-rays in the first detector 1 from the detector 1x that is the first detector in a certain direction and the detector 1y that is the first detector on the approximately opposite side of the detector 1x. Thus, the processing circuitry 105 can cause the specifying function 105a to specify the generation position of the pair annihilation gamma-rays.

Here, description is made of the procedure of estimating the generation position of the pair annihilation gamma-rays from the pair of pieces of first timing information.

The pair annihilation gamma-rays are released to the opposite side due to the relation of momentum conservation along with the pair annihilation of positrons and electrons, and therefore, when Compton scattering or the like is ignored, it is considered that the generation position of the pair annihilation gamma-rays exists on a line connecting the detector 1x and the detector 1y.

Next, when it is assumed that the distance between the detector 1x and the generation position of the pair annihilation gamma-rays is $x_1$, the distance between the detector 1y and the generation position of the pair annihilation gamma-rays is $y_1$, the detection time when the detector 1x has observed the Cherenkov light is $t_1$, the detection time when the detector 1y has observed the Cherenkov light is $t_2$, and the speed of light is c, the difference in detection time between the detector 1x and the detector 1y is the difference in time by which the light advances the difference of distance from the generation position. Thus, $x_1-y_1=c(t_1-t_2)$ is satisfied. In addition, the distance $L_1$ between the detector 1x and the detector 1y is known and the expression $x_1+y_1=L_2$ is satisfied. By setting up these two expressions simultaneously, it is possible to calculate the distance $x_1$ between the detector 1x and the generation position of the pair annihilation gamma-rays, and the distance $y_1$ between the detector 1y and the generation position of the pair annihilation gamma-rays. Therefore, the processing circuitry 105 can cause the specifying function 105a to estimate the generation position and the generation time of the pair annihilation gamma-rays on the basis of the pair of pieces of timing information.

As is understood from the above expressions, when the generation position of the pair annihilation gamma-rays is near the center of the image capture range, the detection time is substantially the same in the detector 1x and the detector 1y, and as the generation position of the pair annihilation gamma-rays is away from near the center of the image capture range, the difference in detection time between the detector 1x and the detector 1y increases. Therefore, the processing circuitry 105 can cause the specifying function 105a to extract the event of the pair annihilation gamma-rays generated within a distance R from the center of the image capture range by extracting the pair annihilation gamma-rays generation event using the trigger that the difference in detection time between the detector 1x and the detector 1y is less than a threshold T.

Incidentally, in the process of extracting the pair annihilation gamma-rays event or the process of estimating the generation position of the pair annihilation gamma-rays in the specifying function 105a of the processing circuitry 105, the response speed of the detector or the variation thereof results in the occurrence of an error. However, it takes shorter after the Cherenkov light is generated from the interaction of the pair annihilation gamma-rays with the light emitter 50 and before the light detection element 51 detects the Cherenkov light in the first detector 1 configured to detect the Cherenkov light than in the second detector 2 configured to detect the scintillation light; therefore, the response speed of the first detector 1 is shorter and the extraction of the pair annihilation gamma-rays event and the estimation of the generation position of the pair annihilation gamma-rays are performed with high accuracy.

Subsequently, at step S110, the second timing information acquisition circuitry 102 acquires the second timing information of the pair annihilation gamma-rays in the second detector 2 in order to specify the event of the pair annihilation gamma-rays in which the first timing information is acquired on the basis of the first timing information acquired at step S100. The processing circuitry 105 causes the specifying function 105a to generate the simultaneous counting information using both the first timing information acquired by the first detector 1 and the second timing information acquired by the second detector 2.

In addition, the second timing information acquisition circuitry 102 transmits the acquired second timing information to the processing circuitry 105 of the console device 20. Here, the second timing information of the pair annihilation gamma-rays in the second detector is the counting information including the scintillator number (P) and the detection time (T), for example. In addition, the second timing information of the pair annihilation gamma-rays in the second detector may be the counting information including the energy value (E) of the pair annihilation gamma-rays having entered the scintillator in addition to those above.

Note that at step S100 and step S110, the first timing information acquisition circuitry 101 and the second timing information acquisition circuitry 102 usually perform the processes at step S100 and step S110 at the same time in parallel instead of performing the processes sequentially.

Note that one example of the detection time (T) is the time when the light detection element 61 of the second detector 2 has observed the scintillation light; however, the embodiment is not limited to this example. In another example, the detection time (T) may be the estimated time of the time when the Cherenkov light is generated by the interaction between the pair annihilation gamma-rays and the scintillator 60 of the second detector 2, the estimated time being estimated based on the time when the light detection element 61 of the second detector 2 has observed the scintillation light. In the second detector 2, the time when the pair annihilation gamma-rays are observed and the second detector 2 observes the scintillation light is a little delayed from the time when the pair annihilation gamma-rays interact with the scintillator 60 of the second detector 2 and the excited state is generated. As described above, the detection time (T) may be either the absolute time or elapsed time since the start of the image capture.

Back to FIG. 4, the second timing information acquisition circuitry 102 acquires a pair of pieces of second timing information of the pair annihilation gamma-rays in the second detector 2 from the detector 2x that is the second detector and the detector 2y that is the second detector on the side substantially opposite to the detector 2x. Thus, in a manner similar to the case of the first detector 1, the processing circuitry 105 can cause the specifying function 105a to estimate the generation position of the pair annihilation gamma-rays.

That is to say, when it is assumed that the distance between the detector 2x and the generation position of the pair annihilation gamma-rays is $x_2$, the distance between the detector 2y and the generation position of the pair annihilation gamma-rays is $y_2$, the detection time when the detector 2x has observed the scintillation light is $t_3$, the detection time when the detector 2y has observed the scintillation light is $t_4$, and the speed of light is c, the difference in detection time between the detector 2x and the detector 2y is the difference in time by which the light advances the difference of distance from the generation position. Thus, $x_2-y_2=c(t_3-t_4)$ is satisfied. In addition, the distance $L_2$ between the detector 2x and the detector 2y is known and the expression $x_2+y_2=L_2$ is satisfied. By setting up these two expressions simultaneously, it is possible to calculate the distance $x_2$ between the detector 2x and the generation position of the pair annihilation gamma-rays, and the distance $y_2$ between the detector 2y and the generation position of the pair annihilation gamma-rays. Therefore, the processing circuitry 105 can cause the specifying function 105a to estimate the generation position and the generation time of the pair annihilation gamma-rays on the basis of the pair of pieces of timing information.

Similarly, as is understood from the above expressions, when the generation position of the pair annihilation gamma-rays is near the center of the image capture range, the detection time is substantially the same in the detector 2x and the detector 2y, and as the generation position of the pair annihilation gamma-rays is away from near the center of the image capture range, the difference in detection time between the detector 2x and the detector 2y increases. Therefore, the processing circuitry 105 can cause the specifying function 105a to extract the event of the pair annihilation gamma-rays generated within the distance R from the center of the image capture range by extracting the pair annihilation gamma-rays generation event using the trigger that the difference in detection time between the detector 2x and the detector 2y is less than the threshold T.

In the process of extracting the pair annihilation gamma-rays event or the process of estimating the generation position of the pair annihilation gamma-rays in the specifying function 105a of the processing circuitry 105, the response speed of the detector or the variation thereof results in the occurrence of an error. Here, in the second detector 2, it takes relatively long after the scintillation light is generated by the interaction of the pair annihilation gamma-rays with the scintillator 60 and before the light detection element 61 detects the generated scintillation light.

However, in the second detector 2, after the pair annihilation gamma-rays interact with the scintillator by the photoelectric effect and before the system returns to the ground state, most part of the energy of the pair annihilation gamma-rays is released again as the scintillation light. Therefore, by counting the number of scintillation light released again, the second timing information acquisition circuitry 102 can acquire the information about the energy of the pair annihilation gamma-rays. At step 5120, the second timing information acquisition circuitry 102 further acquires the energy information of the pair annihilation gamma-rays detected in the second detector 2.

Since the energy of the pair annihilation gamma-rays is 511 keV, which is a predetermined energy corresponding to the rest mass of the positron, if the energy of the observed gamma-rays is largely deviated from the predetermined energy, it can be presumed that the observed gamma-rays are the gamma-rays generated due to Compton scattering or the like. Therefore, the processing circuitry 105 can cause the specifying function 105a to eliminate the scattering event such as Compton scattering using the energy information of the observed gamma-rays.

Subsequently, at step S130, the processing circuitry 105 causes the specifying function 105 to determine whether the first timing information and the second timing information are included in a predetermined time window, thereby determining whether the first timing information and the second timing information are about the same pair annihilation gamma-rays.

Here, in the case where the first timing information and the second timing information are included in the predetermined window, the processing circuitry 105 causes the specifying function 105 to specify that the first timing information and the second timing information are the timing information acquired based on the same pair annihilation gamma-rays and the process advances to step S135.

In one example, in the case where the difference between the generation time of the pair annihilation gamma-rays that is calculated based on the first timing information acquired at step S100 and the generation time of the pair annihilation gamma-rays that is calculated based on the second timing information acquired at step S110 is less than a predetermined threshold and is included in a predetermined time window, the processing circuitry 105 causes the specifying function 105 to specify that the first timing information and the second timing information are acquired based on the same pair annihilation gamma-rays.

Furthermore, only in the case where the difference between the generation position of the pair annihilation gamma-rays that is calculated based on the first timing information acquired at step S100 and the generation position of the pair annihilation gamma-rays that is calculated based on the second timing information acquired at step S110 is less than the predetermined threshold, the processing circuitry 105 may cause the specifying function 105 to specify that the first timing information and the second timing information are acquired based on the same pair annihilation gamma-rays.

In another example, as illustrated in FIG. 4, in the case where the difference between the detection time in the first detector 1 and the detection time in the second detector 2 is included in a predetermined time window, the processing circuitry 105 causes the specifying function 105 to specify that the first timing information and the second timing information are the timing information acquired based on the same pair annihilation gamma-rays. For example, in FIG. 4, in a case where the distance between the detector 1x that is the first detector 1 and the detector 2x that is the second detector 2 is L, the difference $t_3-t_1$ between the detection time $t_1$ in the detector 1x and the detection time $t_3$ in the detector 2x is expected to be about L/c, in which c is the speed of light. Therefore, in a case where the difference between the difference $t_3-t_1$ between the detection time in the first detector 1 and the detection time in the second detector 2 and the time L/c estimated from the distance between the detectors is included in a predetermined time window, the processing circuitry 105 may cause the specifying function 105 to specify that the first timing information and the second timing information are the timing information acquired based on the same pair annihilation gamma-rays.

Subsequently, at step S135, the processing circuitry 105 causes the specifying function 105 to determine whether the acquired energy information is included in the predetermined energy window. Here, the energy of the pair annihilation gamma-rays is always 511 keV regardless of the nuclide at the time of generation. Therefore, in a case where the energy of the observed gamma-rays is much lower than 511 keV, it is possible to determine that the observed gamma-rays are influenced by Compton scattering or the like.

Therefore, by determining whether the acquired energy information is included in the predetermined energy window, the processing circuitry 105 can cause the specifying function 105 to exclude the data influenced by the scattering from the object to be reconfigured.

For example, the processing circuitry 105 can cause the specifying function 105 to determine whether the difference between the estimated energy of the pair annihilation gamma-rays detected in the second detector at step S120 and 511 keV, which is the energy when the pair annihilation gamma-rays are generated, is less than the predetermined threshold and is included in the predetermined energy window.

If the acquired energy information is included in the predetermined energy window (Yes at step S135), the process advances to step S140 and the processing circuitry 105 causes the specifying function 105 to specify that the first timing information and the second timing information are acquired based on the same pair annihilation gamma-rays. On the other hand, if the acquired energy information is not included in the predetermined energy window (No at step S135), the processing circuitry 105 causes the specifying function 105 to determine that the data is influenced by scattering, for example, and excludes this data from the object to be reconfigured.

Thus, when the processing circuitry 105 causes the specifying function 105 to specify the first timing information and the second timing information that are acquired based on the same pair annihilation gamma-rays at step S140, the processing circuitry 105 causes the image generating function 105b to calculate the line of response (LOR) of the pair annihilation gamma-rays on the basis of these pieces of information. For example, in consideration of a possibility that the trajectory of the annihilation gamma-rays is a little displaced on the outside of the first detector 1 compared to the inside of the first detector 1 due to Compton scattering in the first detector 1 as described with reference to FIG. 3B, the processing circuitry 105 causes the image generating function 105b to estimate the line of response (LOR) of the pair annihilation gamma-rays on the basis of the first timing information.

In another example, the processing circuitry 105 may cause the image generating function 105b to estimate the LOR of the pair annihilation gamma-rays on the basis of both the first timing information and the second timing information. Here, the processing circuitry 105 may estimate the scattering angle of Compton scattering in the first detector 1 on the basis of the number of photons of the Cherenkov light detected in the first detector 1, for example, and after correcting the effect of Compton scattering in the first detector 1, estimate the LOR of the pair annihilation gamma-rays on the basis of the first timing information and the second timing information.

Subsequently, the processing circuitry 105 causes the image generating function 105b to generate the medical image on the basis of the LOR estimated for each of the pair annihilation gamma-rays.

Subsequently, as another example, with reference to FIG. 6, description is made of a case in which the processing circuitry 105 causes the specifying function 105a to determine the coincidence using the second timing information first, and then generate the final counting information using the first timing information. The process in FIG. 6 is similar to that in FIG. 5 but the order of steps is different. The process common to that in FIG. 5 is not described below. In FIG. 5 and FIG. 6, the contents of the final process are substantially the same but the order of steps is different, so that the time required in the calculating process may be different, for example. Therefore, whether the process in FIG. 5 is used or the process in FIG. 6 is used is selected depending on the number of events in the first detector 1 and the second detector 2 or the number of scattering events, for example.

First, at step S200, the second timing information acquisition circuitry 102 acquires the second timing information of the pair annihilation gamma-rays in the second detector 2. At step S210, the second timing information acquisition circuitry 120 further acquires the energy information of the pair annihilation gamma-rays detected in the second detector 2. The process at step S200 and S210 is similar to the process at S110 and S120 in FIG. 5.

Subsequently, at step S220, the processing circuitry 105 causes the specifying function 105a to determine the coincidence on the basis of the energy information of the pair annihilation gamma-rays detected in the second detector 2. For example, the processing circuitry 105 causes the specifying function 105a to determine whether the acquired energy information is included in a predetermined energy window, in a manner similar to the process at step S135. In another example, the processing circuitry 105 causes the specifying function 105a to determine whether the difference between the estimated energy of the pair annihilation gamma-rays detected in the second detector and 511 keV, which is the energy when the pair annihilation gamma-rays are generated is less than the predetermined threshold and is included in the predetermined energy window. The processing circuitry 105 determines that the data not included in the predetermined energy window is the data influenced by the scattering and excludes such data from the object to be reconfigured.

On the other hand, if the acquired energy information is included in the predetermined energy window, the processing circuitry 105 causes the specifying function 105a to estimate the generation position and the generation time of the pair annihilation gamma-rays on the basis of the scintillator number (P) and the detection time (T) using the procedure described above with reference to FIG. 5, for example. In addition, for example, the processing circuitry 105 causes the specifying function 105a to extract, as the simultaneous counting information, the event of the pair annihilation gamma-rays generated within the distance R from the center of the image capture range by extracting the pair annihilation gamma-rays generation event using the trigger that the difference in detection time between the opposite detectors in the detector 2 is less than the threshold T.

Subsequently, the first timing information acquisition circuitry 101 acquires the first timing information of the pair annihilation gamma-rays in the first detector 1 at step S230. In addition, the first timing information acquisition circuitry 101 transmits the acquired first timing information to the processing circuitry 105 in the console device 20. Here, the first timing information of the pair annihilation gamma-rays in the first detector is, for example, the detection element number (P) and the detection time (T). The process at step S230 is similar to the process at step S100 in FIG. 5.

Subsequently, at step S240, the processing circuitry 105 causes the specifying function 105a to determine whether the first timing information and the second timing information are included in the predetermined time window, and in a case where the first timing information that is the timing information in the first detector 1 and the timing information in the second detector are included in the predetermined time window (Yes at step S240), the process advances to step S250, and the processing circuitry 105 causes the specifying function 105a to specify that the first timing information that is the timing information in the first detector 1 and the second timing information that is the timing information in the second detector 2 are acquired based on the same pair annihilation gamma-rays. Note that the process at step S240 is similar to the process at step S130.

In this manner, the processing circuitry 105 causes the specifying function 105a to specify the timing information in the first detector corresponding to the event of the pair annihilation gamma-rays detected in the second detector on the basis of the determined coincidence.

In this manner, the processing circuitry 105 causes the specifying function 105a to generate the simultaneous counting information using the first timing information in the first detector 1 and the second timing information in the second detector 2. Here, the simultaneous counting information is the information containing the time and position where the pair annihilation gamma-rays are generated, for example. The processing circuitry 105 causes the image generating function 105b to generate the PET image on the basis of this simultaneous counting information.

In the case of FIG. 6, similar to the case in FIG. 5, in consideration of Compton scattering in the first detector 1, the processing circuitry 105 may cause the image generating function 105b to estimate the line of response (LOR) of the pair annihilation gamma-rays on the basis of the first timing information, or the LOR of the pair annihilation gamma-rays on the basis of both the first timing information and the second timing information.

Subsequently, description is made of the arrangement of the pixels of the first detector 1 and the pixels of the second detector 2.

In the embodiment, the first detector 1 and the second detector 2 may be disposed so that the center lines of a plurality of pixels forming the first detector 1 are displaced from the center lines of a plurality of pixels of the second detector. Here, the center line of each pixel in the first detector 1 means a line connecting centers of pixels corresponding to pixels at symmetric positions with respect to the center of the ring among the pixels forming the first detector 1. Moreover, the center line of each pixel in the second detector means a line connecting centers of pixels corresponding to pixels at symmetric positions with respect to the center of the ring among the pixels forming the second detector 2. Thus, the line of response (LOR) can be estimated more accurately.

Such a circumstance is described with reference to FIG. 7 and FIG. 8.

FIG. 7 is a diagram for describing the estimation of the LOR in a case where the center lines of the pixels 1a, 1b, 1c, 1d, 1e, and if in the first detector 1 coincide respectively with the center lines of the pixels 2a, 2b, 2c, 2d, 2e, and 2f in the second detector 2 as a comparative example. For example, in FIG. 7, the center lines of the pixels 1b and 1e in the first detector 1 coincide with the center lines of the pixels 2b and 2e in the second detector 2.

In this case, it is assumed that a pair of annihilation gamma-rays generated from a generation point Q radiate on a line 70, and along with this, the Cherenkov light is observed in the pixels 1b and 1e in the first detector 1 and the scintillation light is observed in the pixels 2b and 2e in the second detector 2. In this case, the pixels 1b and 1e of the first detector 1 and the pixels 2b and 2e of the second detector 2 exist at the symmetric position with respect to the center of the ring, and are the corresponding pixels.

Here, the center line of the pixels 1b and 1e of the first detector 1, that is, the line connecting the center of the pixel 1b and the center of the pixel 1e and the center line of the pixels 2b and 2e of the second detector 2, that is, the line connecting the center of the pixel 2b and the center of the pixel 2e coincide. Therefore, the direction of the LOR estimated based on the information acquired by the first detector 1 and the direction of the LOR estimated based on the information acquired by the second detector 2 coincide. As a result, the range where the generation of the pair annihilation gamma-rays is estimated based on the information acquired by the first detector 1 is a range 40. In addition, the range where the generation of the pair annihilation gamma-rays is estimated based on the information acquired by the second detector 2 is a range 41. Therefore, both ranges coincide.

Accordingly, a range 42 corresponding to a common part of the range 40 and the range 41 is the range where the generation of the pair annihilation gamma-rays is estimated and the range 42 is relatively wide.

On the other hand, FIG. 8 is a diagram for describing the estimation of the LOR in a case where the center lines of the pixels 1a, 1b, 1c, 1d, 1e, and 1f of the first detector 1 are displaced from the center lines of the pixels 2a, 2b, 2c, 2d, 2e, and 2f of the second detector 2. For example, in FIG. 8, the center lines of the pixels 1b and 1e in the first detector 1 are displaced from the center lines of the pixels 2b and 2e in the second detector 2.

In this case, it is assumed that a pair of annihilation gamma-rays generated from the generation point Q radiate on the line 70, and along with this, the Cherenkov light is observed in the pixels 1b and 1e in the first detector 1 and the scintillation light is observed in the pixels 2b and 2e in the second detector 2. In this case, the pixels 1b and 1e of the first detector 1 and the pixels 2b and 2e of the second detector 2 exist at the symmetric position with respect to the center of the ring, and are the corresponding pixels.

Here, the center line of the pixels 1b and 1e of the first detector 1, that is, the line connecting the center of the pixel 1b and the center of the pixel 1e and the center line of the pixels 2b and 2e of the second detector 2, that is, the line connecting the center of the pixel 2b and the center of the pixel 2e are in the different directions and displaced from each other. Therefore, the direction of the LOR estimated based on the information acquired by the first detector 1 and the direction of the LOR estimated based on the information acquired by the second detector 2 are different from each other. As a result, the range where the generation of the pair annihilation gamma-rays is estimated based on the information acquired by the first detector 1 is the range 40. In addition, the range where the generation of the pair annihilation gamma-rays is estimated based on the information acquired by the second detector 2 is the range 41. Thus, both ranges cover different ranges.

Accordingly, the range 42 corresponding to a common part of the range 40 and the range 41 is the range where the generation of the pair annihilation gamma-rays is estimated and the range 42 is smaller than that in the case of FIG. 7. As a result, the positional resolution of the PET device 100 is improved.

The summary of the embodiment is as below: the radiation diagnosis device according to the embodiment described above performs PET imaging using both the first detector 1 that is the detector configured to detect the Cherenkov light and the second detector 2 that is the detector configured to detect the scintillation light. The detector employing the method of detecting the Cherenkov light has a characteristic of being advantageous in terms of time resolution over the detector employing the method of detecting the scintillation light. On the other hand, the second detector 2 that is the detector configured to detect the scintillation light is inferior to the first detector 1 that is the detector configured to detect the Cherenkov light in terms of the response speed but is advantageous in terms of the energy resolution, and has a characteristic of being able to efficiently remove the scattering event or the like. Therefore, the radiation diagnosis device according to the embodiment generates the counting information using the first detector 1 and the second detector 2. Thus, the counting information in which the high time resolution is maintained while the energy resolution is kept can be generated and therefore, the image quality can be improved.

Other Embodiment

The embodiment is not limited to the aforementioned examples. In the above embodiment, the PET device is described, that is, a pair of annihilation gamma-rays is detected using the first detector 1 and the second detector 2; however, the embodiment is not limited to the example of detecting a pair of annihilation gamma-rays and one gamma-ray may be detected. In addition, the embodiment is not limited to the gamma-rays and is applicable to other radiation such as X-rays. Other examples of the radiation diagnosis device than the PET device to which the embodiment is similarly applicable include single photon emission computed tomography (SPECT) or a Compton camera.

In addition, as illustrated in FIG. 9, in the radiation diagnosis device according to the embodiment, the first detector 1 that is the detector configured to detect the Cherenkov light and the second detector 2 that is the detector configured to detect the scintillation light may be movable detectors. For example, as illustrated in FIG. 9, the first detector 1 may be the movable detector that is movable in a z-axis direction that is a body axis direction perpendicular to the slice plane. Thus, the position of the detector can be moved in accordance with the image capture object, and the image quality can be improved.

In addition, the first detector 1 that is the detector configured to detect the Cherenkov light does not acquire the energy information in the above description; however, the embodiment is not limited to this example and the first detector 1 that is the detector configured to detect the Cherenkov light may acquire the energy information. In one example, the first timing information acquisition circuitry 101 may estimate the energy information of the annihilation gamma-rays on the basis of the angle of the Cherenkov ring obtained by the first detector 1 that is the detector configured to detect the Cherenkov light.

In the above embodiment, the first detector and the second detector are arranged so that the center lines of the pixels forming the first detector 1 are displaced from the center lines of the pixels of the second detector 2; however, the embodiment is not limited to this example. The first detector and the second detector may be arranged so that the center lines of the detector blocks in the first detector 1 are displaced from the center lines of the detector blocks of the second detector 2.

According to at least one embodiment described above, the image quality can be improved.

Regarding the embodiments described above, the following notes are disclosed as aspects and selective characteristics of the invention.

Note 1. A radiation diagnosis device comprising:
a first detector configured to detect Cherenkov light generated when a radiation passes; and a second detector provided to face the first detector on a side farther from a source of generating the radiation and configured to detect energy information of the radiation.

Note 2. The first detector and the second detector are ring-shaped detectors, and a diameter of the first detector is smaller than a diameter of the second detector.

Note 3. The first detector includes a light emitter configured to generate the Cherenkov light as the radiation passes, and the light emitter is thinner than a scintillator provided to the second detector.

Note 4. A pixel size of the light emitter is smaller than a pixel size of the scintillator.

The pixel is the minimum separation unit of the positional resolution of the detector.

Note 5. The radiation is pair annihilation gamma-rays, and the radiation diagnosis device further comprises:

a first timing information acquisition unit configured to acquire first timing information of the pair annihilation gamma-rays in the first detector; and a second timing information acquisition unit configured to acquire second timing information of the pair annihilation gamma-rays in the second detector in order to specify an event of the pair annihilation gamma-rays in which the first timing information is acquired, based on the first timing information.

Note 6. The radiation diagnosis device further comprises a specifying unit configured to specify that the first timing information and the second timing information are acquired based on the same pair annihilation gamma-rays in a case where the first timing information and the second timing information are included in a predetermined time window.

Note 7. The specifying unit is configured to estimate a line of response (LOR) of the radiation, based on the first timing information.

Note 8. The specifying unit estimates an LOR of the radiation by correcting, based on the estimation result at the first detector, the LOR estimated based on the detection result at the second detector.

Note 9. The specifying unit estimates an LOR of the radiation taking Compton scattering at the first detector into consideration.

Note 10. The specifying unit estimates an LOR of the radiation based on the number of photons of Cherenkov light detected at the first detector.

Note 11. The specifying unit estimates a scattering angle of Compton scattering at the first detectors and estimates an LOR of the radiation based on the scattering angle.

Note 12. The second timing information acquisition unit is configured to further acquire energy information of the pair annihilation gamma-rays in the second detector, and the specifying unit is configured to specify that the first timing information and the second timing information are acquired based on the same pair annihilation gamma-rays in a case where the energy information is included in a predetermined energy window.

Note 13. The radiation is pair annihilation gamma-rays, and the radiation diagnosis device further comprises a specifying unit configured to determine coincidence, based on the energy information and timing information of the pair annihilation gamma-rays detected in the second detector, and specify the timing information in the first detector corresponding to an event of the pair annihilation gamma-rays detected in the second detector, based on the determined coincidence.

Note 14. The specifying unit is configured to specify that the timing information in the first detector and the timing information in the second detector are acquired based on the same pair annihilation gamma-rays in a case where the timing information in the first detector and the timing information in the second detector are included in a predetermined time window.

Note 15. A detector column length of the first detector is shorter than a detector column length of the second detector.

Note 16. The light emitter is formed of a medium that suppresses scintillation by the radiation compared to the scintillator of the second detector.

Note 17. The medium is bismuth germanium oxide (BGO) or a lead compound.

Note 18. The first detector and the second detector are arranged so that center lines of a plurality of pixels forming the first detector are displaced from center lines of a plurality of pixels forming the second detector.

Here, the center line of each pixel in the first detector 1 means a line connecting centers of pixels corresponding to pixels at symmetric positions with respect to the center of the ring among the pixels forming the first detector 1. Moreover, the center line of each pixel in the second detector means a line connecting centers of pixels corresponding to pixels at symmetric positions with respect to the center of the ring among the pixels forming the second detector 1.

Note 19. The first detector is a movable detector.

Note 20. The first detector is a detector that is movable in a z-axis direction corresponding to a body axis direction that is perpendicular to a slice plane.

Note 21. A positron emission tomography (PET) device comprising:

a first detector configured to detect Cherenkov light generated when a radiation passes; and a second detector provided to face the first detector on a side farther from a source of generating the radiation and configured to detect energy information of the radiation.

Note 18. A radiation diagnosis method to be performed by a radiation diagnosis device, the radiation diagnosis method comprising:

detecting, with a first detector, Cherenkov light that is generated when a radiation passes; and detecting, with a second detector, energy information of the radiation, the second detector being provided to face the first detector on a side farther from a source of generating the radiation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation diagnosis device, comprising:

a first detector configured to detect Cherenkov light generated when Tall radiation passes; and a second detector provided to face the first detector on a side farther from a source of generating the radiation, and configured to detect energy information of the radiation.

2. The radiation diagnosis device according to claim 1, wherein
the first detector and the second detector are ring-shaped detectors, and
a diameter of the first detector is smaller than a diameter of the second detector.

3. The radiation diagnosis device according to claim 2, wherein
the radiation is consists of pair-annihilation gamma-rays, and
the radiation diagnosis device further comprises:
first timing information acquisition circuitry configured to acquire first timing information of the pair-annihilation gamma-rays in the first detector; and
second timing information acquisition circuitry configured to acquire second timing information of the on pair-annihilation gamma-rays in the second detector in order to specify an event of the pair-annihilation gamma-rays in which the first timing information is acquired, based on the first timing information.

4. The radiation diagnosis device according to claim 3, further comprising:
processing circuitry configured to specify that the first timing information and the second timing information are acquired based on the same pair-annihilation gamma-rays when the first timing information and the second timing information are included in a predetermined time window.

5. The radiation diagnosis device according to claim 4, wherein the processing circuitry is further configured to estimate a line of response (LOR) of the radiation, based on the first timing information.

6. The radiation diagnosis device according to claim 5, wherein the processing circuitry is further configured to estimate the line of response (LOR) of the radiation by correcting, based on a detection result of the first detector, a line of response (LOR) estimated based on a detection result of the second detector.

7. The radiation diagnosis device according to claim 5, wherein
the second timing information acquisition circuitry is configured to further acquire the energy information of the pair-annihilation gamma-rays in the second detector, and
the processing circuitry is further configured to specify that the first timing information and the second timing information are acquired based on the same pair-annihilation gamma-rays when the energy information is included in a predetermined energy window.

8. The radiation diagnosis device according to claim 2, wherein
the radiation is consists of pair-annihilation gamma-rays, and
the radiation diagnosis device further comprises processing circuitry configured to
determine coincidence, based on the energy information and timing information of the pair-annihilation gamma-rays detected in the second detector, and
specify the timing information in the first detector corresponding to an event of the gamma-rays detected in the second detector, based on the determined coincidence.

9. The radiation diagnosis device according to claim 2, wherein a detector column length of the first detector is shorter than a detector column length of the second detector.

10. The radiation diagnosis device according to claim 1, wherein the first detector includes a light emitter configured to generate the Cherenkov light as the radiation passes,
the second detector includes a scintillator, and
the light emitter of the first detector is thinner than the scintillator of the second detector.

11. The radiation diagnosis device according to claim 10, wherein a pixel size of the light emitter is smaller than a pixel size of the scintillator.

12. The radiation diagnosis device according to claim 10, wherein the light emitter comprises a medium that suppresses a scintillation by the radiation.

13. The radiation diagnosis device according to claim 1, wherein tie first detector and the second detector are arranged so that center lines of a plurality of pixels forming the first detector are displaced from center lines of a plurality of pixels forming the second detector.

14. A radiation diagnosis method to be performed by a radiation diagnosis device, the radiation diagnosis method comprising:
detecting, with a first detector, Cherenkov light that is generated when radiation passes; and
detecting, with a second detector, energy information of the radiation, the second detector being provided to face the first detector on a side farther from a source of generating the radiation.

* * * * *